United States Patent [19]

Brown

[11] Patent Number: 5,236,082
[45] Date of Patent: Aug. 17, 1993

[54] NEEDLE SHIELD DEVICE FOR SURGICAL PACKAGES

[75] Inventor: David L. Brown, Wallingford, Conn.

[73] Assignee: United States Surgical Corporation, Norwalk, Conn.

[21] Appl. No.: 636,227

[22] Filed: Dec. 31, 1990

[51] Int. Cl.⁵ .......................................... A61L 17/02
[52] U.S. Cl. ...................................... 206/63.3; 206/382
[58] Field of Search ................... 206/63.3, 380, 382, 206/363

[56] References Cited

U.S. PATENT DOCUMENTS

| | | | |
|---|---|---|---|
| 2,993,589 | 7/1961 | Zoller et al. | 206/63.3 |
| 3,136,418 | 6/1964 | Stacy et al. | 206/63.3 |
| 3,444,994 | 5/1969 | Kaepernik et al. | 206/63.3 |
| 3,857,484 | 12/1974 | Thyen | 206/63.3 |
| 3,939,969 | 2/1976 | Miller et al. | 206/63.3 |
| 4,063,638 | 12/1977 | Marwood | 206/63.3 |
| 4,120,395 | 10/1978 | Mandel et al. | 206/63.3 |
| 4,249,656 | 2/1981 | Cerwin et al. | 206/63.3 |
| 4,253,563 | 3/1981 | Komarnycky . | |
| 4,284,194 | 8/1981 | Flatau . | |
| 4,391,365 | 7/1983 | Batchelor . | |
| 4,406,363 | 9/1983 | Aday | 206/63.3 |
| 4,412,614 | 11/1983 | Ivanor et al. | 206/63.3 |
| 4,413,727 | 11/1983 | Cerwin et al. | 206/63.3 |
| 4,427,109 | 1/1984 | Roshdy | 206/63.3 |
| 4,483,437 | 11/1984 | Cerwin et al. . | |
| 4,491,218 | 1/1985 | Aday | 206/63.3 |
| 4,496,045 | 1/1985 | Ferguson et al. | 206/63.3 |
| 4,555,016 | 11/1985 | Aday et al. | 206/63.3 |
| 4,572,363 | 2/1986 | Alpern . | |
| 4,574,948 | 3/1986 | Huck et al. | 206/63.3 |
| 4,708,241 | 11/1987 | Black . | |
| 4,884,681 | 12/1989 | Roshdy et al. . | |
| 4,896,767 | 1/1990 | Pinheiro | 206/63.3 |

Primary Examiner—Bryon P. Gehman
Attorney, Agent, or Firm—Thomas R. Bremer; Peter G. Dilworth; Rocco S. Barrese

[57] ABSTRACT

A needle shield for suture-needle assemblies constructed of a fibrous material and foldable about at least two score lines to provide a protective device against needle damage and accidental sticking of the user's fingers.

29 Claims, 4 Drawing Sheets

NEEDLE SHIELD DEVICE FOR SURGICAL PACKAGES

BACKGROUND OF THE INVENTION

1. Field of the Invention

The present invention relates to surgical suture-needle packages, and more particularly to a needle shield device for protecting the tip of the needles from damage and to eliminate the possibility of accidental sticking of a person's finger by the needles.

2. Discussion of the Prior Art

Packaging devices for needles and suture needle assemblies which include protective flaps or covers are well known in the art. These packages generally include a fold over flap or cover which encloses the needles or the needle tips in the package. In many cases, the flap is integrally formed as part of the package so that the flap or cover comprises a tear away portion which exposes the needles upon opening of the package.

Several tear away type needle covers for use with surgical suture-needle assembly packages are provided in the prior art. These packages generally comprise a panel having either perforations or score lines which facilitate tearing a portion of the panel from the package to expose the needles after the package is opened. After the tear away cover or flap is removed, the needle and suture assembly may be removed from the package in the conventional manner.

In the prior art, several packages having tear away cover flaps are disclosed, such as U.S. Pat. No. 4,063,638 to Marwood. The package disclosed in Marwood comprises a three panel package, where the suture is wound and held at the center panel and the needle is held in an outer panel. A panel having the tear away flap is provided on the outer panel opposite the needle retaining panel, and the tear away flap is folded over the sutures followed by the needle retaining flap. Upon opening the package, the flap is torn away, thus revealing the needle so that the needle may be removed in the conventional manner.

U.S. Pat. No. 4,406,363 to Aday, U.S. Pat. No. 4,412,614 to Ivanov et al., and U.S. Pat. No. 4,427,109 to Roshdy disclose tear away flaps or covers similar to that disclosed in Marwood above.

Another type of package prevalent in the prior art provides a fold over flap which covers the needles within the package. When the package is opened, the fold over flap is unfolded to reveal the needles so that the needles may be removed in the conventional manner. Such a device is disclosed in U.S. Pat. No. 4,574,948 to Huck et al. Huck et al. provides a packaging device in which the suture-needle assembly is secured on one panel of the package and the needles are secured on a second panel. A fold over flap is provided to cover the needles to prevent sticking of the user and to prevent damage to the needle tips. As the package is opened, the fold over flap is unfolded to reveal the needles so that the needles may be removed in a conventional manner. A similar type device is disclosed in U.S. Pat. No. 4,708,241 to Black.

Other fold over cover flaps for packaging devices are disclosed in U.S. Pat. No. 4,120,395 to Mandel et al., U.S. Pat. No. 4,391,365 to Batchelor, and U.S. Pat. No. 4,884,681 to Roshdy et al. Mandel et al. and Roshdy et al. disclose a cover flap to which the needles are attached, so that as the flap is folded over the needles are folded with it to cover and protect the needles. Batchelor discloses a device similar to Huck et al. above.

The devices disclosed in the prior art suffer from several disadvantages in which the risk of accidental sticking of the needle into the fingers of the user is not significantly reduced or eliminated, and further, many of these devices suffer the disadvantage in that the cost of packaging is increased due to the necessity for additional packaging material as well as increasing the number of packaging steps during assembly.

Surgical suture-needle assembly packages and needle packages are generally constructed of a material which resists folding and bending and which is strong enough to hold a coiled suture in place without the risk of the suture unraveling during shipment. The package must also be rigid enough to resist bending or folding to eliminate the risk of creasing the suture during shipment, so that when the package is opened the suture may be removed from the package without creases or bends. There is significant emphasis in the surgical suture industry placed on the "memory" retention of the suture material, so that the suture retains its original shape upon removal from the package with a minimum of bends and creases, even after extended periods of time within the package. In view of this, many of the packages disclosed above which provide a needle retaining member which is folded over the package increase the amount of bends in the suture material during packaging, which may lead to an undesirable suture-needle assembly upon removal from the package.

A further disadvantage of the prior art packages is that in using the package itself to protect the needles, such as those packages disclosed above having a tear away portion, there is a requirement that additional packaging material must be provided to cover the needle. Given the fact that many of these packages employ rigid panels, sometimes in laminate form, the cost of packaging is necessarily increased to provide the needle cover. In addition, the step of forming the packaging material must include the addition of score lines or perforations to facilitate the tear feature to expose the needles.

An additional disadvantage to these fold over devices lies in the fact that the needles are hidden from view until that portion of the package is either torn away or unfolded to reveal the needles. Consequently, the user is at risk of accidentally sticking himself with the needles since he cannot see the needles during the tear away or unfolding step.

The novel needle shield device for surgical packages having needles or suture-needle assemblies of the present invention obviates the disadvantages encountered in the prior art and provides a universal needle shield device for use with any surgical needle or suture-needle assembly package which is of light weight material and which provides the user with protection against sticking while further providing protection for the needle tips against damage. The needle shield of the present invention may be used with any surgical needle or suture-needle assembly package, and eliminates the requirement for providing additional packaging material and the requirement for complex folding arrangements of the rigid packaging material to cover the needles.

SUMMARY OF THE INVENTION

The present invention provides a novel needle shield device for surgical packages having needles or suture-needle assemblies packaged therein. The device may also be used with syringes or hypodermic-type needles to protect the needle and to guard against sticking during opening of the package, by allowing the user to view the needle during the opening procedure so that the user knows at all times where the sharp tips of the needles are located.

The needle shield of the present invention essentially comprises a sheet of fibrous material which is attachable to a cover panel of the needle or suture-needle assembly package in the vicinity of the tips of the needles, and is preferably secured by adhesives, glue or the like.

The needle shield of the present invention has a substantially rectangular shape, and is provided with a series of score lines or fold lines along the edges of the rectangle from which outwardly directed projections extend. Along one edge, a series of fork-like projections extend from the needle shield, and it is at this location that the needle shield is secured to the cover panel of the package of needles. Preferably, an adhesive-backed foam needle park or retainer is secured across the fork-like projection and then is secured directly to the package in the area of the needle tips. The spaces between the fork-like projections allow the cover panel of the adhesive-backed needle park to adhere to the package. In this manner, the needles are retained in the needle park so that their tips lie on the fibrous material which forms the needle shield.

Intermediately spaced between the edge having the fork-like projections and the opposite parallel edge, is a scored line which forms a first fold line of the needle shield and which is parallel to the edge forming the forked projections. Preferably, two additional scored fold lines are provided which are perpendicular to the first scored line and the edge of the device having the forked projections. It is these two scored lines, preferably parallel to each other, which form the side edges of the needle shield. Wing-like projections extend outwardly from the scored lines which are folded about the body of the shield in a manner described below.

In use, the foam needle park is positioned across the fork projections and the needle shield and foam park are adhered to cover panel of the package adjacent the needles. The needles are then positioned in the needle park so that the tips of the needles lie on the needle shield. The shield is then folded over itself at the first scored line, to wrap the body of the shield about the needle tips. The wing-like projections are then folded along the perpendicular side score lines under the bottom of the sheet to hold the needle shield about the needle tips.

It is also contemplated that the needle shield be provided with an end guard member which comprises a projection which extends upwardly from the edge of the needle shield opposite the fork projections so that when one of the side wing-like extensions is folded under the needle shield, the fold line extends through this projection so that the shield is wrapped about the suture-needle connection point of the endmost suture-needle assembly.

The present invention provides a needle shield which may be used with any type of needle package, whether the needles be for use in a suture-needle assembly, a hypodermic-type syringe needle, or the like. The fibrous material which comprises the needle shield is preferably a material such as Tyvek (a registered trademark of DuPont), which is constructed of polyolefin fibers which are bonded by heat and calender pressure. While this is the preferred material, other, similar fibrous materials such as pressed paper or fiberboard are also contemplated for use as the needle shield of the present invention. The scored fold lines may also be perforated lines which may facilitate easier folding and unfolding.

BRIEF DESCRIPTION OF THE DRAWINGS

The features of the present invention will become more readily apparent and may be understood by referring to the following detailed description of an illustrative embodiment of the needle shield for surgical packages and its novel construction, taken in conjunction with the accompanying drawings in which.

DETAILED DESCRIPTION OF THE PREFERRED EMBODIMENTS

Figure 1:
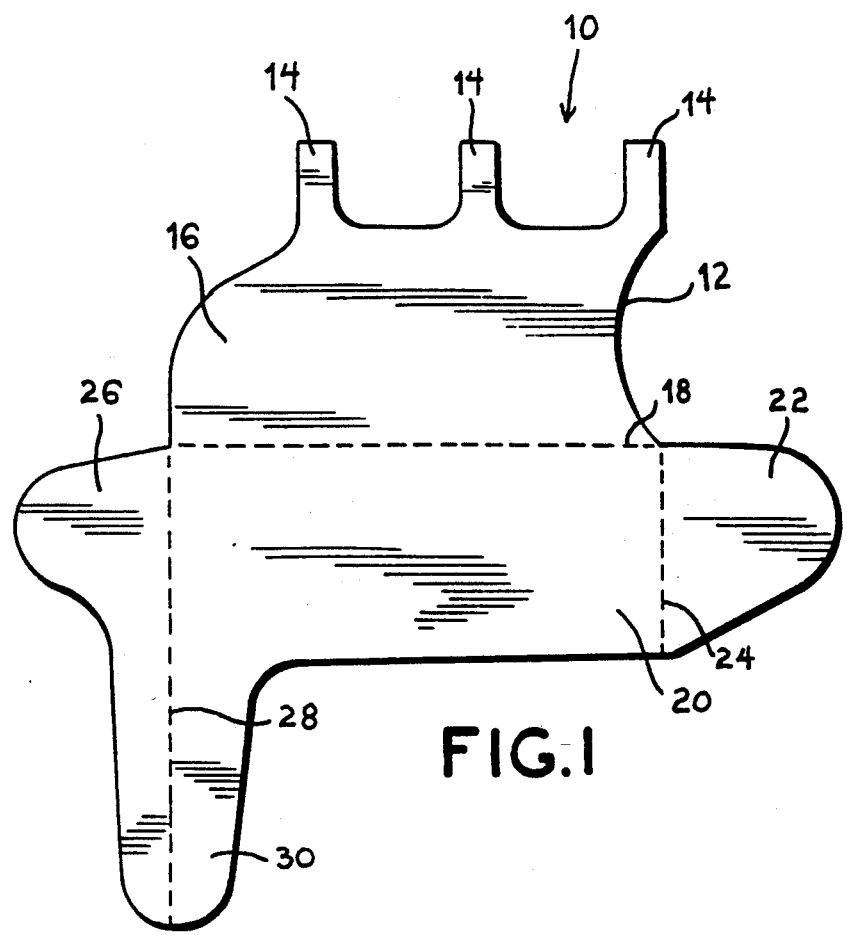
FIG. 1 illustrates a top plan view of a needle shield according to the present invention.

Referring now in specific detail to the drawings, in which like reference numerals identify similar or identical elements throughout the several views, FIG. 1 shows the needle shield 10 of the present invention. Needle shield 10 comprises a flat sheet of fibrous material, preferably a non-woven fibrous sheet such as Tyvek (a registered trademark of DuPont) which comprises spun bonded polyolefin fibers pressed together to form a sheet of fibrous material. While it is contemplated in the preferred embodiment that needle shield 10 be constructed of Tyvek, it is clear that any fibrous material may satisfy the requirements for protecting packaged needles from damage and eliminating the possibility of accidental sticking of a person's finger by the needles.

The body portion 12 of needle shield 10 is provided with a series of fork-like projections 14 which extend outwardly from body 12 and are spaced from each other as shown. A score line 18 is provided on body 12 which essentially separates body 12 into two halves. Bottom half 16 and top half 20 are described in more detail in relation to FIGS. 2 and 3.

Wing-like projections 22 and 26 extend outwardly from body 12 and are further defined by score line 24 which allows projection 22 to be folded onto body 12, and score line 28 which allows projection 26 to be likewise folded. A third projection 30 is provided along the edge of top sheet 20 opposite the edge defined by score line 18. Projection 30 will be described in more detail below in reference to FIGS. 2 and 3.

Figure 2:
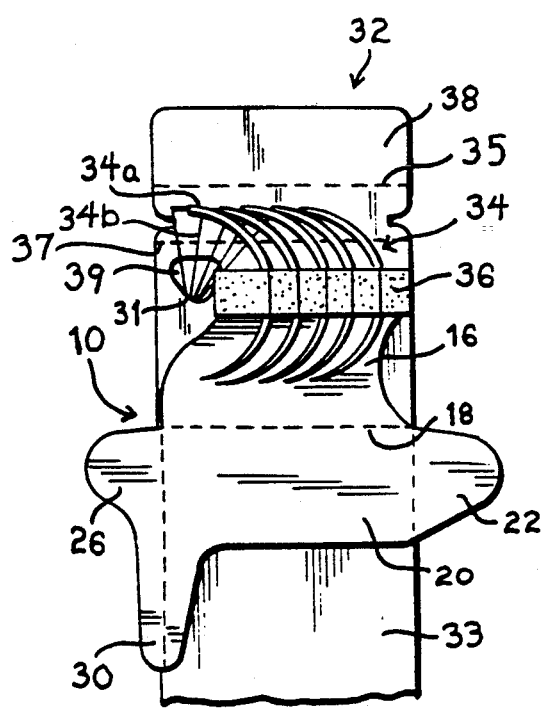
FIG. 2 illustrates the needle shield of FIG. 1 positioned on a suture-needle package in the open position to reveal the needles of the package.

Turning now to FIG. 2, a suture-needle package 32 is shown having needle shield 10 positioned on cover panel 33. Package 32 may comprise any suture-needle retainer, having at least top or cover panel 33 and a bottom panel 39 over which cover panel 33 is secured, so that the sutures 34b of assemblies 34 are positioned between panels 33 and 39. Cover panel 33 is provided with aperture 31, through which bottom panel 39 is visible. The sutures 34b suture-needle assemblies 34 extend through aperture 31 and terminate in needles 34a. Needle shield 10 is preferably secured to cover panel 33 of package 32 in the vicinity of needle assemblies 34, so that the tips of the needles rest on bottom sheet 16. To secure needle shield 10 to package 32, any adhesives or glue materials may be used. However, it is preferred that an adhesive backed needle retaining member, such as foam needle park 36 be provided to secure needle shield 10 to cover panel 33 of package 32. Needle park 36 is provided with an adhesive backing which secures the needle shield 10 to the back of needle park 36 at projections 14. The spacing between projections 14 allows the needle park to be further secured to cover panel 33 of package 32 so that needle shield 10 is secured to cover panel 33 of the package between cover panel 33 and foam needle park 36. Needle park 36 also provides a means for holding the needle assemblies 34 in position, which assists needle shield 10 in protecting the tips of the needles from damage and protects a user from accidental sticking.

Figure 3:
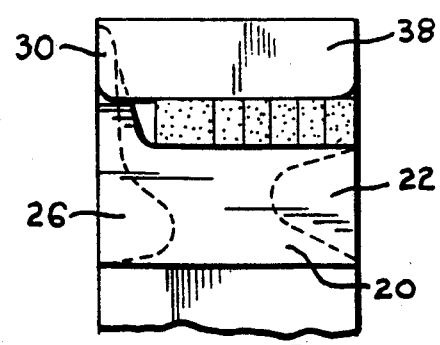
FIG. 3 illustrates the needle shield of FIG. 2 in the closed position.

In use, after needle shield 10 has been secured to cover panel 33 the package through needle park 36, a needle assemblies 34 are secured in needle park 36 so that the tips of the needles rest on bottom sheet 16 as shown in FIG. 2. Needle shield 10 is then folded on score line 18 so that top sheet 20 covers the tips of the needles as shown in FIG. 3. Needle shield 10 is so dimensioned that the upper edge of top sheet 20 engages the front edge of needle park 36 to completely enclose the tips of the needles. At this point, wing-like projections 22 and 26 are folded along score lines 24 and 28, respectively, and tucked under bottom sheet 16 to hold needle shield 10 in place. Projection 30 is provided to cover the suture connection to the endmost needle assembly 34a as been seen in FIG. 3. Finally, top flap 38 of suture package 32 is folded at perforated line 35 over the suture ends of needle assemblies 34 to completely enclose the needles as shown in FIG. 3. A second perforated line 37 is provided to allow the top flap 38 and upper portion of suture package 32 to be folded over in the open position to provide 360° access to the needles 34 from the front, as to cover panel 33, or back, as from bottom panel 39, of the package, so that the needles may be removed from either side of the package.

Figure 4:
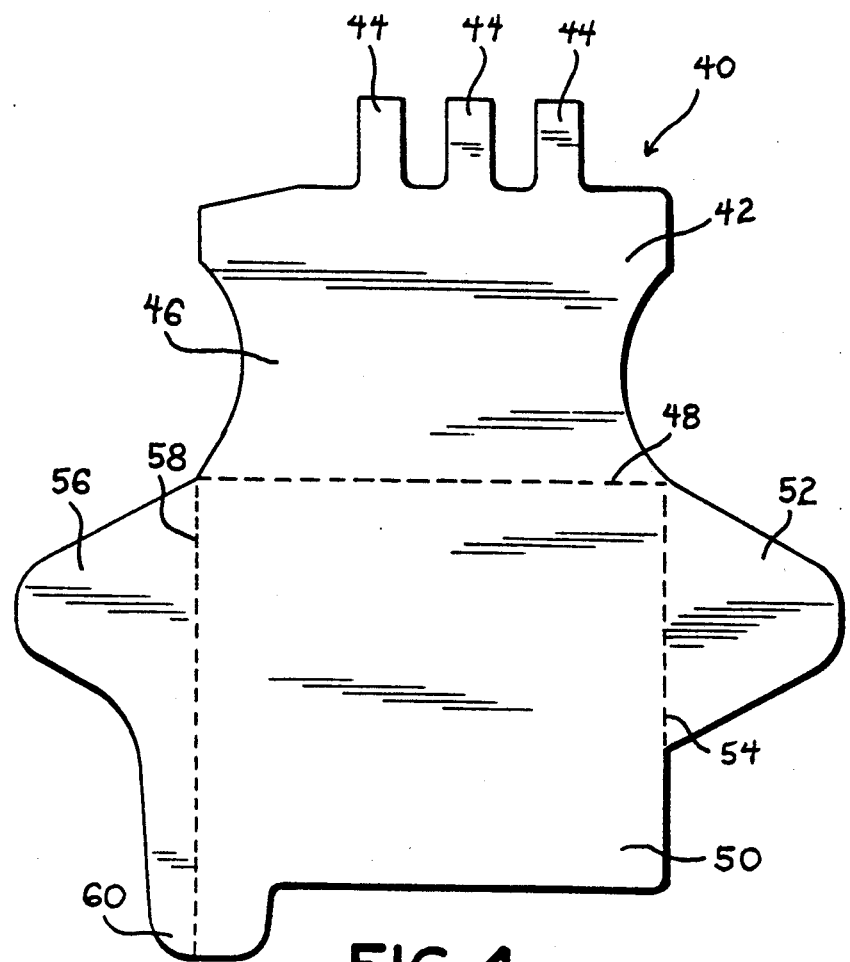
FIG. 4 illustrates a top plan view of an alternate embodiment of the needle shield of the present invention.

Turning now to FIG. 4, needle shield 40 is an alternate embodiment of needle shield 10 of FIG. 1. A sheet of fibrous material 42 is provided having fork-like projections 44 which are spaced from each other as shown. A score line 48 is provided to allow sheet 42 to be folded over itself in much the same manner as shown in relation to FIG. 1. Folding needle shield 40 along score line 48 provides a bottom sheet 46 and a top sheet 50, where top sheet 50 has wing-like projections 52 and 56 which are defined by score lines 54 and 58, respectively. A further projection 60 is provided along the upper edge of top sheet 50, and projection 60 will be described further below in reference to FIGS. 5 and 6.

Figure 5:
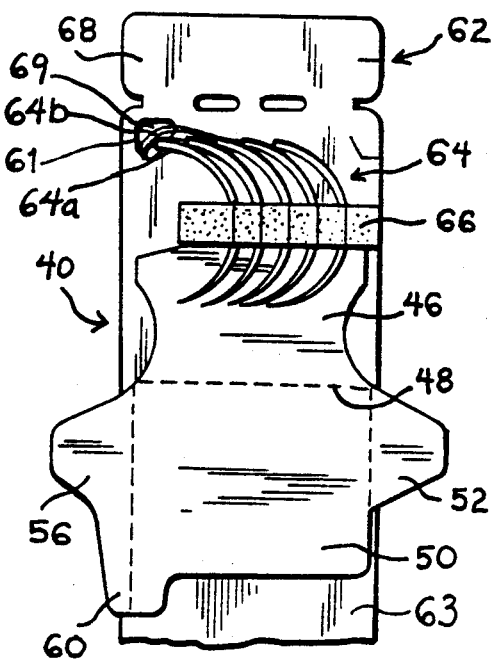
FIG. 5 illustrates the needle shield of FIG. 4 positioned on a suture-needle package in the open position.

As best seen in FIG. 5, needle shield 40 is positioned on a cover panel 63 of suture-needle package 62 in the vicinity of needle assemblies 64.

Package 62 may comprise any suture-needle retainer, having at least top or cover panel 63 and a bottom panel 69 over which cover panel 63 is secured, so that the sutures 64b of assemblies 64 are positioned between panel 63 and 69. Cover panel 63 is provided with aperture 61, through which bottom panel 69 is visible. The sutures 64b of assemblies 64 extend through aperture 61 and terminate in needles 64a. Needle shield 40 is secured to cover panel 63 of package 62 through the provision of an adhesive backed foam needle park 66 which is similar to needle park 36 as shown in FIG. 2. Again, needle shield 40 is secured to cover panel 63 of the package between the adhesive backed needle park 66 and the face of package 62, where the needle park 66 secures shield 40 to cover panel 63 of the package to hold fork-like projections 44 in place. Needle assemblies 64 are then secured in needle park 66 as seen in FIG. 5.

Figure 6:
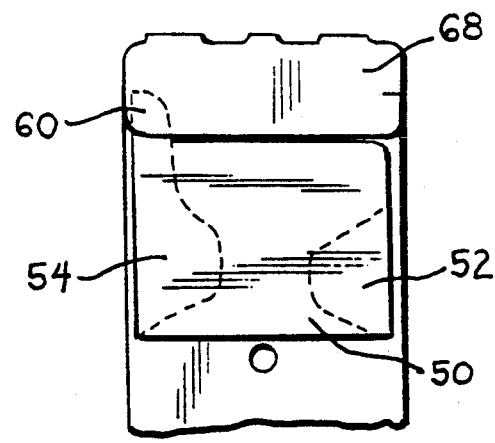
FIG. 6 illustrates the needle shield of FIG. 5 positioned on a suture-needle package in the fully closed position.

In use, after needle shield 40 is secured to cover panel 63 of package 62, needle assemblies 64 are positioned in needle park 66 so that the tips of needle assemblies 64 rest on bottom sheet 46. Needle shield 40 is then folded at score line 48 so that top sheet 50 covers the needle tips which are now positioned between top sheet 50 and bottom sheet 46. As seen in FIG. 6, score line 48 is so positioned that when needle shield 40 is folded at score line 48, the upper edge of top sheet 50 completely covers needle park 66. At this point, wing-like projections 52 and 56 are folded on score lines 54 and 58, respectively, and tucked under bottom sheet 46 to secure the needle shield. As been seen in FIG. 6, upper projection 60 provides a protective cover for the suture end of endmost needle assembly 64a. Finally, top flap 68 of package 62 is folded over the suture ends of the needle assemblies 64 to completely enclose the needles as shown.

Figure 7:
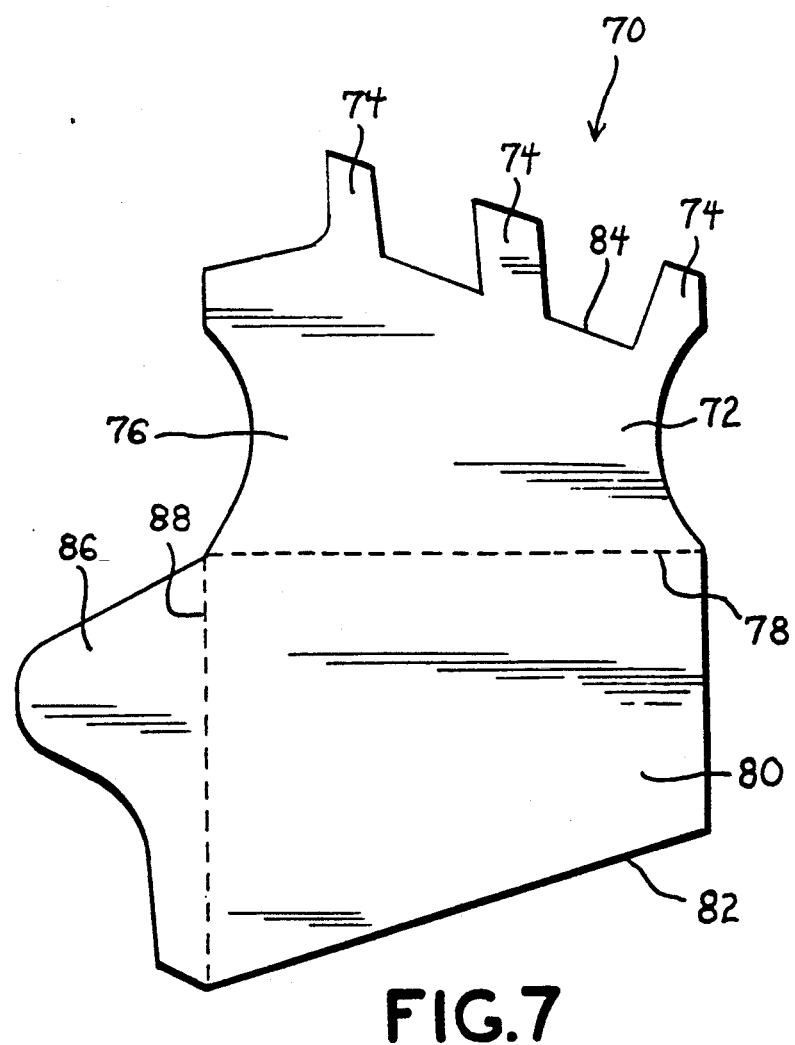
FIG. 7 illustrates a top plan view of a further embodiment of the needle shield of the present invention.

Turning now to FIG. 7, a further alternate embodiment of the needle shield is shown. Needle shield 70 is constructed of a sheet of fibrous material 72 having fork-like projections 74 which are spaced from each other along top edge 84. A score line 78 is provided which allows sheet 72 to be folded over on itself to define bottom sheet 76 and top sheet 80. A wing-like projection 86 is provided which is foldable about score line 88 which will be described below.

Figure 8:
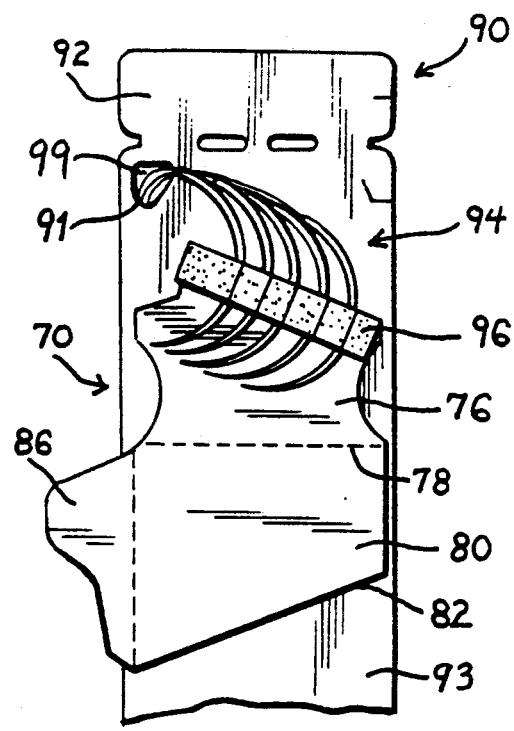
FIG. 8 illustrates the needle shield of FIG. 7 in position on a suture-needle package in the open position.

As best seen in FIG. 8, needle shield 70 is positioned on a suture-needle package 90 through the provision of an adhesive backed foam needle park 96. Foam needle park 96 secures needle shield 70 to cover panel 93 of package 90 in much the same manner as described above in reference to FIGS. 2 and 5. In this embodiment, upper edge 84 is positioned at an angle to score line 78, and needle park 96 is positioned along upper edge 84 to secure needle shield 70 through fork-like projections 74. After needle shield 70 is secured to package 90, needle assemblies 94, which are positioned between cover panel 93 and bottom panel 99, and which extend through aperture 91, are secured in needle park 96 as shown. Bottom panel 99 is visible through aperture 91 in cover panel 93.

Figure 9:
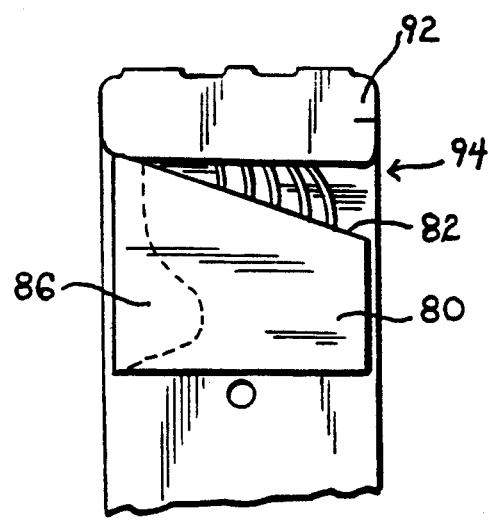
FIG. 9 illustrates the needle shield of FIG. 8 in position on a suture-needle package in the closed position.

In use, needle assemblies 94 are positioned in needle park 96 so that the tips of the needles are positioned on bottom sheet 76. Needle shield 70 is then folded on score line 78 so that the needle tips are positioned between bottom sheet 76 and top sheet 80. Edge 82 of top sheet 80 is angled relative to score line 78 so that when top sheet 80 is folded onto bottom sheet 76, edge 82 is aligned with the edge of foam needle park 96 as best seen in FIG. 9. At this point, wing-like projection 86 is folded about score line 88 and tucked under bottom sheet 76 to secure the needle shield about the needle. Flap 92 is then folded down onto the suture ends of the needles to secure the needles therein while providing a view of the needles as best seen in FIG. 9.

While the invention has been particularly shown and described with reference to the preferred embodiments, it will be understood by those skilled in the art that various modifications and changes in form and detail may be made therein without departing from the scope and spirit of the invention. Accordingly, modifications such as those listed above, but not limited thereto, are to be considered within the scope of the invention.

What is claimed is:

1. A needle shield in combination with a surgical suture-needle retainer, said retainer including at least a cover panel and a bottom panel having a plurality of sutures positioned therebetween, said shield comprising a sheet of fibrous material having a plurality of scored lines to facilitate folding of said sheet of material about a plurality of needles attached to said sutures and positioned on one of said panels of said retainer, said shield including means for securing said sheet of material to one of said panels adjacent said needles, said scored lines being positioned such that said shield is positioned on one of said panels and encloses said needles upon folding of said sheet of material.

2. The combination according to claim 1, wherein said scored lines comprise compressed areas forming creases in said material.

3. The combination according to claim 1, wherein said scored lines comprise perforations in said material.

4. The combination according to claim 1, wherein said scored lines comprise a pair of parallel lines intersected by at least one perpendicular line.

5. The combination according to claim 1, wherein said means for securing said sheet of material to one of said panels includes a plurality of parallel projections extending away from said shield, said projections having gaps therebetween.

6. The combination according to claim 5, wherein said projections are secured to one of said panels by adhesives.

7. The combination according to claim 5, wherein said projections are secured to one of said panels by an adhesive backed needle holding member, said holding member being positioned perpendicular to said projections and parallel to an end of said shield opposite said projections.

8. A needle shield in combination with a surgical suture-needle package, said package including at least a cover panel and a bottom panel having a plurality of sutures positioned therebetween, said shield comprising a sheet of fibrous material having a plurality of scored lines to facilitate folding of said sheet of material about a plurality of needles attached to said sutures and positioned on one of said panels of said package, said shield including means for securing said sheet of material to one of said panels adjacent said needles such that said shield is positioned on one of said panels, said scored lines being positioned such that said shield encloses said needles upon folding of said sheet of material, wherein a first fold line facilitates folding of said sheet of material over onto itself to form a top sheet and a bottom sheet, and second and third scored lines, parallel to each other and perpendicular to said first scored line, each to facilitate folding of an extension of said sheet of material under said bottom sheet to enclose said needles within said shield.

9. The combination according to claim 8, wherein one of said extensions extends above an upper edge of said shield when said shields is in the folded position, said extension facilitating shielding of at least one needle of said suture-needle package.

10. A needle cover shield in combination with in a surgical suture-needle package, said package including a plurality of suture-needle assemblies, said package having a front panel and a back panel forming an envelope enclosing said suture-needle assemblies therebetween with needles positioned on one of said panels and exposed adjacent a top edge of said panel, said needle shield comprising a sheet of fibrous material positioned on and secured to said front panel of said package at a first edge adjacent said needles, said sheet having a plurality of fold lines for facilitating folding of said sheet about said needles to form said shield, wherein first and second parallel fold lines are positioned perpendicular to said first edge adjacent said needles, and a third fold line is positioned parallel to said first edge and perpendicular to said first and second lines, such that said sheet is foldable over itself at said third line to form a top sheet and a bottom sheet, and further foldable at said first and second lines to form a pocket for enclosing said needles therein.

11. The combination according to claim 10, wherein said first and second fold lines define outwardly directed extensions in said sheet of fibrous material, said extensions being foldable under said bottom sheet of said shield to enclose said needles therein.

12. A needle cover shield in combination with a surgical suture-needle retainer, said retainer including a plurality of surgical suture-needle assemblies, said retainer having a front panel and a back panel forming an envelope enclosing said suture-needle assemblies therebetween with needles positioned on one of said panels and exposed adjacent a top edge of said panels, said needle shield comprising:

a sheet of fibrous material positioned on and secured to said front panel of said retainer at a first edge adjacent said needles, said sheet having a plurality of fold lines for facilitating folding of said sheet about said needles to form said shield.

13. The combination according to claim 12, wherein said sheet of fibrous material includes a series of projections extending outwardly from said sheet, said projections being secured to said front panel of said retainer.

14. The combination according to claim 13, wherein said projections are secured to said front panel by an adhesive-backed needle holding member.

15. The combination according to claim 12, wherein said sheet of fibrous material includes a projection adjacent an edge opposite said first edge for shielding at least one needle of said retainer.

16. In combination, a blank for a needle cover shield and a surgical suture-needle retainer, said retainer including at least a cover panel and a bottom panel for retaining a plurality of sutures therebetween, said blank comprising:

a sheet of fibrous material, said sheet having a substantially rectangular shape forming a top edge and a bottom edge and two side edges, said top edge having a plurality of projections forming a forked portion with spacing between each projection, said bottom edge having an outwardly directed extension adjacent one of said side edges extending away from said blank, and said side edges each having outwardly directed extensions intermediate said top and bottom edges extending away from said blank, wherein said blank is secured to one of said panels of said retainer at said forked portion.

17. The combination according to claim 16, wherein said outwardly directed extensions on said side edges are defined by scored fold lines.

18. The combination according to claim 17, wherein one of said scored fold lines extends through said outwardly directed extension of said bottom edge.

19. The combination according to claim 16 wherein a scored fold line is provided parallel to and intermediate between said top and bottom edges.

20. A method for loading suture-needle assemblies into a retainer, said retainer including a bottom panel and a cover panel, comprising the steps of:
positioning a needle shield on said retainer at an upper edge of said cover panel, said needle shield comprising a sheet of fibrous material having a plurality of fold lines for facilitating folding of said sheet about needles of said suture-needle assemblies;
attaching said needle shield to said cover panel;
positioning at least one suture-needle assembly between said bottom panel and said cover panel such that a needle of said assembly is positioned on one of said panels of said retainer on said fibrous sheet; and
folding said sheet at said fold lines to form an envelope about said needle.

21. A method according to claim 20, wherein said step of folding said sheet at said fold lines about said needle includes the step of positioning an end of said needle adjacent to an upper edge of said shield and said panel to facilitate removal of said needle.

22. A method according to claim 20, further comprising the step of attaching a needle holding member adjacent said needle shield to hold said needle in place within said shield when said shield is in a folded condition.

23. A method according to claim 22, wherein said needle holding member is positioned on said shield.

24. A method according to claim 20, wherein said step of attaching said shield to cover said panel comprises attaching an adhesive-backed needle holding member to an edge of said shield and to cover panel to hold said shield in place.

25. A method according to claim 24, wherein said needle shield includes a plurality of forked projections extending from an edge of said shield having spaces therebetween, said needle holding member being secured to said cover panel across said projections.

26. A method according to claim 20, wherein said needle shield is folded about a first fold line to fold said sheet over onto itself to form a top sheet and a bottom sheet, and is further folded about second and third fold lines parallel to each other and perpendicular to said first fold line to fold extensions of said sheet under said bottom sheet to form a pocket to enclose said needles therein.

27. A suture retainer comprising:
a bottom panel;
a cover panel including at least one aperture;
a plurality of sutures positioned between said cover panel and said bottom panel, said sutures extending through said aperture such that a plurality of needles attached to said sutures are positioned on said cover panel; and
a needle shield for enclosing said needles, said shield being positioned on and attached to said cover panel and being folded to enclose said needles therein.

28. A suture retainer according to claim 27, wherein said needle shield comprises a sheet of fibrous material and having a plurality of fold lines to facilitate folding of said material about said needles.

29. A suture retainer according to claim 27, wherein said needle shield includes means for securing said needles to said shield.

* * * * *